(12) United States Patent
Tapper (10) Patent No.: US 6,223,076 B1
(45) Date of Patent: Apr. 24, 2001

(54) SWEAT CONTROL SYSTEM

(76) Inventor: Robert Tapper, 1935 Armacost Ave., Los Angeles, CA (US) 90025

(*) Notice: Subject to any disclaimer, the term of this patent is extended or adjusted under 35 U.S.C. 154(b) by 0 days.

(21) Appl. No.: 09/271,007

(22) Filed: Mar. 17, 1999

Related U.S. Application Data (63) Continuation-in-part of application No. 08/876,111, filed on Jun. 13, 1997, which is a continuation of application No. 08/336,327, filed on Nov. 8, 1994, now abandoned, which is a continuation of application No. 08/160,401, filed on Dec. 1, 1993, now abandoned, which is a continuation-in-part of application No. 08/150,550, filed on Nov. 8, 1993, which is a continuation of application No. 07/995,927, filed on Dec. 22, 1992, now abandoned, which is a continuation of application No. 07/781,330, filed on Oct. 22, 1991, now abandoned, which is a continuation-in-part of application No. 07/776,766, filed on Oct. 15, 1991, now abandoned, which is a continuation-in-part of application No. 07/607,874, filed on Nov. 1, 1990, now Pat. No. 5,224,927.

(51) Int. Cl.$^7$ ....................................................... A61N 1/30
(52) U.S. Cl. ............................................. 604/20; 604/501
(58) Field of Search ..................... 604/20, 501; 424/449; 514/947

(56) References Cited

U.S. PATENT DOCUMENTS

| 3,054,405 | 9/1962 | Tapper . |
| 4,325,367 | * 4/1982 | Tapper . |

(List continued on next page.)

FOREIGN PATENT DOCUMENTS

| 41 37 960 A1 | 5/1993 | (DE) . | |
| 0060452 | 9/1982 | (EP) . | ..................................... (EP) . |

(List continued on next page.)

OTHER PUBLICATIONS

PCT/ US00/06860—International Search Report from EPO, Jul. 2000.
European Search Report for EPO Application EP91118776 Mar. 1992.

(List continued on next page.)

*Primary Examiner*—Mark Bockelman
(74) *Attorney, Agent, or Firm*—Fulwider Patton Lee & Utecht, LLP (57) ABSTRACT

A sweat control or hyperhidrosis treatment device for providing iontophoresis of antiperspirant into a region of a human body includes a DC power source, a controller and a pair of electrodes. The electrodes are mounted in generally close proximity to one another and are separated by an insulating member. The electrodes generally carry an antiperspirant element and are responsive to an a current signal through the controller. The electrodes are generally formed of aluminum and have a rough surface to increase the number of aluminum ions available for infusion into the region. The controller converts the DC signal to an AC waveform. The electrodes are of opposite polarity with respect to each other such that during the first portion of the AC waveform, current is conducted through the region in a first direction from the first electrode to the second electrode. During the second portion of the AC waveform, current is conducted through the region in a second direction from the second electrode to the first electrode. The device further includes a pair of pads. Each of the pads is positioned in adjacent contact with one of the electrodes and preferably carries sodium salicylate to increase the permeability of the region. The electrodes are sized and arranged so that the tissue to be treated can extend across the insulating member and simultaneously contact both of the pads. The pads generally carry an aluminum-based antiperspirant such as aluminum-chlorohydrate or aluminum-zirconium or may include an anticholinergic substance.

56 Claims, 5 Drawing Sheets

U.S. PATENT DOCUMENTS

| | | |
|---|---|---|
| 4,340,047 | 7/1982 | Tapper et al. . |
| 4,406,658 | 9/1983 | Lattin et al. . |
| 4,474,570 * | 10/1984 | Ariura et al. . |
| 4,640,689 | 2/1987 | Sibalis . |
| 4,702,732 | 10/1987 | Powers et al. . |
| 4,786,277 | 11/1988 | Powers et al. . |
| 4,808,152 | 2/1989 | Sibalis . |
| 4,816,261 * | 3/1989 | Luebbe et al. . |
| 4,931,046 | 6/1990 | Newman . |
| 4,963,367 | 10/1990 | Ecanow . |
| 4,973,303 | 11/1990 | Johnson et al. . |
| 5,006,108 | 4/1991 | La Prade . |
| 5,008,111 | 4/1991 | Boder .................................. 424/449 |
| 5,013,293 | 5/1991 | Sibalis . |
| 5,019,034 | 5/1991 | Weaver et al. . |
| 5,023,085 | 6/1991 | Francoeur et al. . |
| 5,042,975 | 8/1991 | Chien et al. . |
| 5,047,007 | 9/1991 | McNichols et al. . |
| 5,224,927 * | 7/1993 | Tapper . |

FOREIGN PATENT DOCUMENTS

| | | |
|---|---|---|
| 0097436 | 1/1984 | (EP) . |
| 0230153 | 7/1987 | |
| 0309093 | 3/1989 | (EP) . |
| 2 030 453 | 3/1980 | (GB) . |
| 2206493 | 1/1989 | (GB) . |
| 2219510A | 12/1989 | (GB) . |

OTHER PUBLICATIONS

Research Disclosure No. 29504 on Method for Multiple Drug Delivery via Iontophoresis—Lattin et al.—Abstract Only.

Research Disclosure No. 29520 on Method to Control Delivery of Uncharged Drugs via Iontophoresis—Gary A. Lattin, Nov. 1988—Abstract Only.

Journal of Pharmaceutical Sciences, vol. 67, No. 10, Oct. 1989, Conductivity of Drugs used for Iontophoresis—Gangarosa et al—pp. 1439–1443.

Controlled Release Society, Inc., 17th Int'l Symposium on Controlled Release of Bioactive Materials on Important Parameters Affecting Iontophoretic Transdermal Delivery of Insulin—Sun et al., Jul. 1990—pp. 202–203.

Skin Permeability, 9. Iontophoresis—Shaefer et al., 1982—1 page (page number unknown). numeral 9.

Clayton's Electrotherapy and Actinotherapy—Scott, 1980—pp. 139–140 only.

Studies on Iontophoresis, I. Experimental Studies on the Causes and Prevention of Iontophoretic Burns—Molitor et al., Dec. 1939—pp. 779–785.

Excerpt from the Federal Register, vol. 44, No. 168, Aug. 28, 1979—Proposed Rules—pg. 50521.

Electrotherapy—Wolf, 1981—pp. 106–109.

Medical Research Engineering, Oct.–Nov. 1971, Low Voltage, Direct Current Plethysmograph Burns—Leeming et al.—pp. 19–21.

JAMA, Nov. 30, 1970, vol. 214, No. 9, Low–Voltage, Direct–Current Burns—Leeming et al.—pp. 1681–1684.

A Manual of Electrotherapy, The Direct Current and Ion Transfer—Watkins, Third Edition—pp. 125–127.

Journal of Pharmaceutical Sciences, vol. 78, No. 5, May 1989, Iontophoretic Delivery of Model Inorganic & Drug Ions—Lattin et al.—pp. 365–369.

Journal of Controlled Release, 11 (1990), In Vitro and in Vivo Evaluation of Trans Dermal Iontophoretic Delivery of Hydromophone—Lattin et al.—pp. 123–185.

The Journal of Orthopaedic & Sports Physical Therap, Introduction of Antiinflammatory Drugs by Iontophoresis: Double Blind Study—Bertolucci, 1982—pp. 103–108.

Pediatrics 48:(5) 831–832, Nov. 1971, Low Voltage Skin Burns—Jarvis et al.

Cutis, vol. 26, Aug. 1980, Treatment of Hyperhidrosis by Tap Water Iontophoresis—Levit—pp. 192–194.

Arch Derm, vol. 98, Nov. 1968, Simple Device for Treatment of Hyperhidrosis by Iontphoresis—Levit—pp. 505–507.

British Journal of Dermatology (1977) 96, 189, Tap Water Iontophoresis in Palmo–Plantar Hyperhydrosis—Shrivastava et al.—pp. 189–195.

Mechanism of Action of Iontophresis in the Treatment of Palmar Hyperhidrosis—Hill et al., Jul. 1981—pp. 69–72.

Poldine Iontophoresis in the Treatment of Palmar and Plantar Hyperhidrosis—Aust. J. Derm. (1976), 17, 92—Hill—pp. 92–93.

American Journal of Physical Medicine, vol. 31, Jun. 1952, No. 3, The Treatment of Hyperhidrosis of Hands and Feet with Constant Current—Bouman et al.—pp. 158–169.

Iomed's Newsletter, Phoresor Phorum, Choosing the Right Drugs, Jan. 1990—p. 2 only.

Iontophoretic Delivery of Drugs: Fundamentals, Developments and Biomedical Applications—Banga et al.—p. 12 only.

Ionic Medication in Dermatology—Shaffer, 1930—pp. 303–304.

Journal of the APTA, vol. 43, No. 8, The Iontophoresis of $C_{21}$ Esterified Blucocorticoids: Preliminary Report—Murray et al.—pp. 579–580.

Transdermal Drug Delivery—Burnette—p. 252 only.

Iontophoretic Transport of a Homologous Series of Ionized & Nonionized Model Compounds: Influence of Hydrophobicity & Mechanistic Interpretation—Del Terzo et al., 1989—Title of article only.

Increased Penetration of Nonelectrolytes Into Mouse Skin During Iontophoretic Water Transport (Iontohydrokinesis)—Gangarosa et al., Nov. 1979—pp. 377–381.

Iontophoretic Delivery of Drugs: Fundamentals, Developments and Biomedical Applications,—Banga et al.—pp. 2 and 5.

Therapeutic Electricity and Ultraviolet Radiation—Harris, 1967.

Electrophoretic Therapy—Harpuder—one page (page number unknown).

Transdermal Drug Delivery Development Issues and Research Initiatives, Chapter 11, Iontophoresis—Burnette—p. 248 only.

Penetration of Surface Tissues with Copper by Iontophoresis—Penetration with Organic and Inorganic Copper Salts and the use of Detergents in Iontophoresis—Pereyra—pp. 96–105.

Soap/Cosmetics/Chemical Specialities, Amphoteric Surfactants—A Structure Function Study—Bilbo et al., Apr. 1990—pp. 46, 49–50, 115–116.

American Journal of Emergency Medicine, vol. 13, No. 1, Jan. 1995, Lidocaine via Iontophoresis in Laceration Repair: A Preliminary Safety Study—Ernst et al.—pp. 17–19.

Soap/Cosmetics/Chemical Specialties, Sep. 1993, Hydroxy Acid and Skin Aging—Smith—pp. 54, 56–58, 76.

* cited by examiner

SWEAT CONTROL SYSTEM

This application is a continuation-in-part of U.S. Ser. No. 08/876,111 filed Jun. 13, 1997, which is a continuation application of U.S. Ser. No. 08/336,327 filed Nov. 8, 1994 now abandoned, which is a continuation application of U.S. Ser. No. 08/160,401 filed Dec. 1, 1993 now abandoned, which is a continuation-in-part of U.S. Ser. No. 08/150,550 filed Nov. 8, 1993 pending, which is a continuation of U.S. Ser. No. 07/995,927 filed Dec. 22, 1992 now abandoned, which is a continuation of U.S. Ser. No. 07/781,330 filed Oct. 22, 1991 now abandoned, which of U.S. Ser. No. 07/776,766 filed Oct. 15, 1991 now abandoned, which is a continuation-in-part of U.S. Ser. No. 07/607,874 filed Nov. 1, 1990 now U.S. Pat. No. 5,224,927 issued Jul. 6, 1993.

BACKGROUND OF THE INVENTION

This invention relates generally to a hyperhidrosis treatment device, and more particularly, to a method and apparatus for conveniently and quickly providing enhanced iontophoretic application of antiperspirant chemicals to regions of the human body in a simple and economic manner.

Treatment of excess sweating is commonly done in one of two ways. For individuals with a mild case of sweating, effective treatment may be had through the application of chemical antiperspirants. For those inflicted with a more severe case of excess sweating or even hyperhidrosis, iontophoretic treatment may be necessary. Iontophoretic treatment involves the electrical introduction of ions into the skin to block the sweat duct.

An iontophoretic device for the treatment of hands, palms and axilla is disclosed in U.S. Pat. No. 4,325,367. In this device a support structure houses a pair of aluminum alloy electrodes in generally close proximity to one another as well as a source of electrical power. The electrodes are arranged so that, for example, the palm of a hand can be placed on the device and simultaneously contact both electrodes. A moisture absorbing pad is interposed between each of the electrodes and the skin of the user. In operation, the pads are moistened with water and the user places his hand on the pads. Current is applied from the electrodes, through the pads, to the user, thereby providing iontophoretic treatment.

Another iontophoretic device is disclosed in U.S. Pat. No. 5,224,927. In this device, the electrical current applied between a pair of electrodes is periodically reversed at very low frequencies to mitigate tissue damage. Again, a moisture absorbing pad is interposed between each of the electrodes and the skin of the user. In operation, the treatment site may be prepared using an appropriate ionic surfactant such as an amphoteric or a cationic surfactant and electrical current in the form of a low frequency AC signal is applied to the treatment area through either water moistened pads or ionicsurfactant moistened pads.

In the well known DRIONIC compact iontophoretic device, which employs various aspects of both U.S. Pat. Nos. 4,325,367 and 5,224,927, long term treatment of severe cases of hyperhidrosis is provided through a series of iontophoretic treatments. The mean-average treatment time to effectively stop sweat is approximately seven hours. The treatment regimen calls for a series of approximately half-hour individual treatment sessions spread over the course of several days. The actual length of a session and time between sessions depends on the user's tolerance to electric current. During each treatment, metal ions, e.g., aluminum ions from the electrodes, are driven deep into the eccrine sweat pores to stop sweat. The cumulative effect of the series of treatments may stop sweat for up to six weeks. Moreover, the DRIONIC device relies on amplified voltages of 60 volts and safety control circuits.

While the DRIONIC device is intended for the extremely heavy sweater, the use of such a formidable and time consuming device may be an undesirable treatment for people suffering from only a mild case of excess sweating. Most of these individuals will chose the daily use of a wide variety of well-known over-the-counter topical antiperspirants to control heavy sweating. However, a problem associated with over-the-counter topical antiperspirants is the lack of sufficient penetration into the skin of the eccrine-pore-blocking antiperspirant chemical. Thus these topical antiperspirants have limited efficacy. It has been reported that over-the-counter topical antiperspirants are effective for only about fifty percent of those who use them. The those other fifty percent receive little or no benefit from such antiperspirants. In those people who enjoy some benefit from store bought antiperspirants, this efficacy is only between twenty and forty percent.

Hence, there has been a long existing need in the art for a system capable of administering deep-penetrating iontophoretic application of antiperspirant chemicals to the human body in a short period of time. There also exists a need for such a device that operates at a low power rating and thus relatively independent of a user's tolerance for electrical current. There further exists a need for such a device that is conducive to daily use. The present invention fulfils all of these needs and others.

SUMMARY OF THE INVENTION

Briefly, and in general terms, the present invention is directed to improvements in the treatment of excess sweating and hyperhidrosis through the use of an iontophoresis administration of antiperspirant chemicals into the human body.

In a first aspect, the present invention embodies a sweat treatment device for effecting iontophoresis at a specified region of tissue. The device includes a source of electric current, a controller and a pair of electrodes. The electrodes are mounted in generally close proximity to one another and are separated by an insulating member. The electrodes carry an antiperspirant element and are responsive to the source of electrical current through the controller. One of the electrodes is connected to the source of electrical current and is arranged to act primarily as a cathode. The other electrode is connected to the source of electrical current and is arranged to act primarily as an anode. The device further includes a pair of pads. Each of the pads is positioned in adjacent contact with one of the electrodes and carries sodium salicylate. The electrodes are sized and arranged so that the tissue to be treated can extend across the insulating member and simultaneously contact both of the pads.

By carrying an appropriate salt of salicylic acid, such as sodium salicylate, the pads provide for enhanced permeability of the tissue being treated. The sodium salicylate increases the permeability of the tissue and facilitates electrical driving of the ions contained in the antiperspirant elements carried by the electrodes deeper into the tissue to precipitate the skin protein and stop sweat. Thus the device provides increase efficacy. The salicylic salt and antiperspirant chemicals would typically be replaceable.

In a more detailed aspect of the invention, the pads further carry an aluminum-based antiperspirant. In another facet, the pad antiperspirant consists of one of either aluminum-chlorohydrate or aluminum-zirconium. In yet another aspect, the electrodes are formed of sheet stock metal having an irregular, nonsmooth, surface. This nonsmooth surface creates a greater overall surface area on the electrode thereby increasing the number of antiperspirant ions available for infusion by ionthophoresis. In still another facet, the sheet stock metal consists of aluminum, aluminum alloy, magnesium or magnesium alloy. In yet another aspect, the electrodes comprise sandblasted sheet stock metal. On other aspects the electrodes comprise powered metal formed on the sheet stock metal and the electrodes comprise aluminum oxide.

In another facet, the invention is related to an enhanced device for applying iontophoresis treatment to a selected region of a biological subject. The device includes first and second electrodes mounted in generally close proximity to one another and separated by an insulating member. The device also includes a pair of pads, each positioned in adjacent contact with one of the electrodes. Each of the pads carry an antiperspirant. The electrodes are sized and arranged so that the region to be treated can extend across the insulating member and simultaneously contact both of the pads. The device further includes an electrical energy source for conducting an electrical current through the region in a first direction from the first electrode to the second electrode; and a controller for intermittently reversing, at a relatively low frequency which prevents skin damage, between approximately 20 times per second and approximately once every three minutes, the polarity of the electrodes to cause the electrical current to flow in a second direction opposite to the first direction.

By including antiperspirant in the pads and by reversing the polarity of the electrodes to reverse the direction of current flow through the region of treatment, the device provides for a greater infusion of antiperspirant ions into the region in a set amount of time. The reason for this is that if a positively charged antiperspirant is carried by a pad when the positive half of the AC signal is driving the electrode associated with the pad, then the positive component of the antiperspirant is repelled and driven into the skin.

In more detailed facets of the invention, the antiperspirant is aluminum based. In another aspect, the antiperspirant consists of one of either aluminum-chlorohydrate or aluminum-zirconium. In still another facet, the percentage of aluminum-chlorohydrate or aluminum-zirconium contained within the antiperspirant is greater than 2%. In yet another facet, the pad further carries sodium salicylate. In a further aspect, the antiperspirant comprises an anticholinergic.

In a third aspect, the invention is related to an applicator for providing the chemical materials necessary to affect iontophoresis treatment to a selected region of a biological subject. The applicator is responsive to an AC waveform provided by a generator. The applicator includes first and second electrodes mounted in generally close proximity to one another. The electrodes are separated by an insulating member and are responsive to the AC waveform. The applicator also includes a pair of pads. Each of the pads is positioned in adjacent contact with one of the electrodes and carries an antiperspirant. The electrodes are sized and arranged so that the region to be treated can extend across the insulating member and simultaneously contact both of the pads.

In more detailed facets of the invention, the first and second electrodes are responsive to the AC waveform such that the electrodes are of opposite polarities. In another aspect, the pads comprise a material containing the antiperspirant. In a still another facet, the pads are formed of a fiber and the antiperspirant is saturated into the pads. In other aspects, the antiperspirant comprises aluminum based chemicals and the antiperspirant comprises an anticholinergic.

In a fourth facet, the invention is related to a method of iontophoretic infusion of antiperspirant substances into a biological subject. The method comprises the step of locating a pair of electrically conductive electrodes adjacent a surface of the subject to be treated. The method also includes the steps of placing at least one antiperpirant substance and a suitable salt of salicylic acid, such as sodium salicylate, between at least one of the electrodes and the surface of the subject to be treated, and conducting an electrical current through the surface of the subject for a set duration of time. The current passes through the surface in a first direction from a first of the electrodes to a second of the electrodes on the subject. The method further includes the step of periodically and regularly reversing, at a relatively low frequency, between approximately 20 times per second and approximately once every three minutes, the polarity of the electrodes to cause the electrical current to flow in a second direction opposite to the first direction.

In a more detailed aspect of the invention, the set time duration for treatment is between 10 and 20 seconds and the low frequency is such that the polarity of the electrodes is reversed at least once during the set time duration.

These and other objects, aspects and advantages of the present invention will become apparent from the following more detailed description, when taken in conjunction with the accompanying drawings which illustrate, by way of example, the preferred embodiments of the invention.

DETAILED DESCRIPTION OF THE PREFERRED EMBODIMENTS

Figure 1:
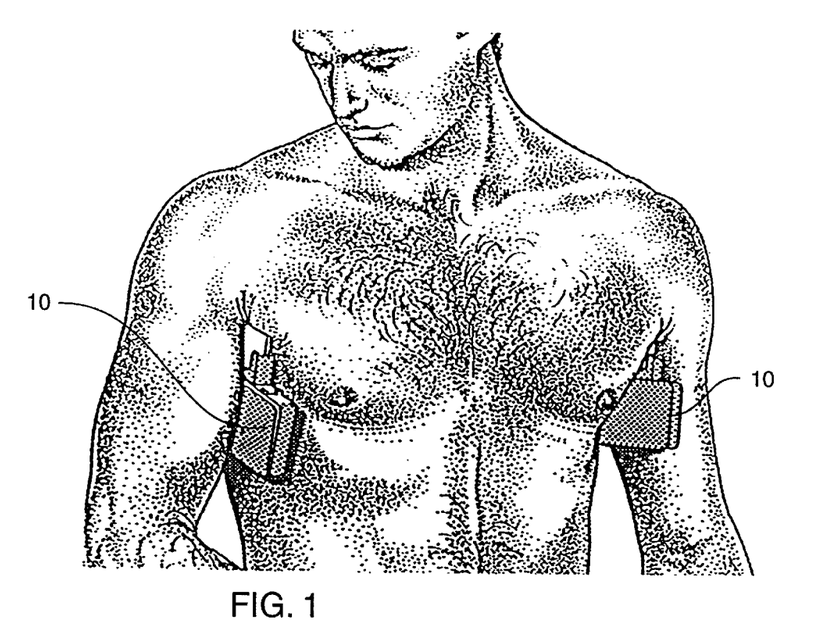
FIG. 1 illustrates an iontophoretic treatment device including a generator and an applicator constructed in accordance with the invention, and shown positioned in the axilla area of a human subject.

Referring now to the drawings, and more particularly to FIG. 1, there is shown an iontophoretic treatment device 10, of relatively simple, economical, reliable and compact construction, embodying features of the present invention. The iontophoretic treatment device 10 is shown in use in the axilla area of a suitable biological subject so that the device contacts the skin of the subject for appropriate administration of antiperspirant chemicals by iontophoretic delivery.

While the iontophoretic device 10 is shown in a presently preferred self-contained embodiment, it will be appreciated by those of ordinary skill in the art that a larger structural and/or physical packaging unit (not shown) may be utilized, including a terminal electrode applicator for contact with the skin, and also embodying various features of the present invention.

With reference to FIGS. 2 through 5, in accordance with the present invention, an iontophoretic treatment device 10 is provided which includes an applicator 20 and a generator 39. The applicator 20 includes a pair of metallic electrodes 12, 14 mounted on a retainer 16. While the electrodes 12, 14 may be made of any metal, in a preferred embodiment they are formed of aluminum or aluminum alloy sheet stock. In another embodiment the electrodes are formed of magnesium or magnesium alloy sheet stock. In a preferred embodiment, the surface of the electrodes 12, 14 are treated to create more surface area such that more aluminum ions are available to inhibit sweat. This may be done, for example, by sandblasting the electrode 12, 14 surface or making the electrodes from powered metal. Aluminum oxide may also be added to the electrodes 12, 14. The electrodes may also be replaceable as a disposable unit.

Figure 2:
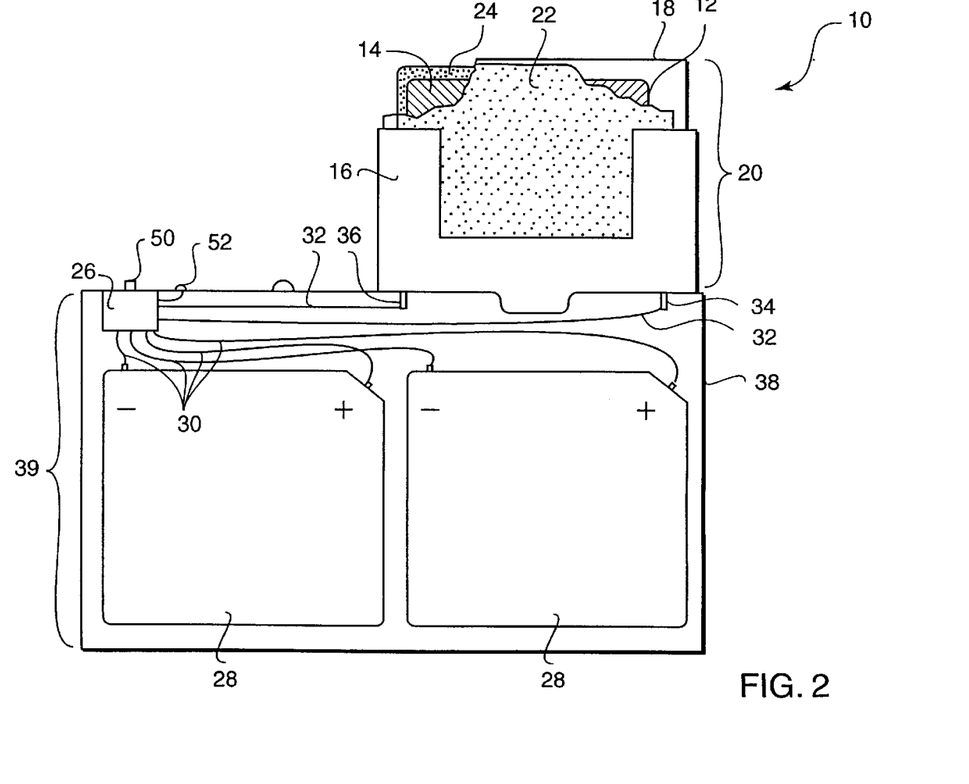
FIG. 2 is a plan view of a presently preferred embodiment of the iontophoretic device of FIG. 1, with a side cover of the generator being removed and portions of the applicator being broken away to illustrate internal structure.

The electrodes 12, 14 are in generally close proximity to one another and lie in generally parallel planes. The electrodes 12, 14 are separated by a relatively narrow insulating member 18. To prevent inadvertent short circuiting of the device 10 when in use, the insulating member 18 is of sufficient height to separate the pads 22, 24. Moreover, a retainer 16 is configured to ensure that no moisture from the pads 22, 24 can flow across the insulating member 18 and cause a short circuit. With this arrangement, the iontophoretic treatment device 10 can be positioned in the axilla area and held in place during treatment by the user simply lowering his arm. This arrangement has a significant advantage over prior devices in that the user's hands are relatively free during treatment, making this device particularly convenient to use.

The applicator 20 further includes a pair of moisture absorbing pads 22, 24. The pads 22, 24 are interposed between skin of the region being treated and the electrodes 12, 14 to ensure adequate electrical contact with the treatment region being treated and to distribute that electrical contact over a greater area of the region. While the pads 22, 24 can be of any suitable porous synthetic or natural fiber material, it has been found that a polyester material is preferred. Polyester electrode pads soak up water much more readily than do pads made of wool felt. In addition, polyester pads do not exhibit the tendency to shrink, as do wool pads. Moreover, polyester pads are much more economical to supply, and do not support bacterial life as readily as wool felt pads.

As further explained hereinafter, the pads 22, 24 carry antiperspirant chemicals which, in combination with the aluminum electrodes, provide the ions to penetrate the skin to effectively block the sweat ducts. By "carry" it is meant that the pads are either 1) formed of a material containing the subject chemicals, 2) that the pads are formed of an absorbent material, such as felt, and are pre-soaked with the subject chemicals or 3) a combination of 1) and 2). In a preferred embodiment, the pads carry aluminum chlorohydrate or aluminum-zircomium. In another preferred embodiment, the pads carry an anticholinergic. In addition to the antiperspirant chemicals, the pads may also carry an appropriate salt of salicylic acid, such as sodium salicylate, to enhance aluminum ion skin penetration or permeability and hence efficacy of the device. Sodium salicylate has also been shown to have healing properties.

The generator 39 portion of the iontophoretic treatment device 10 includes an electronics package comprising an AC current generating chip 26, a battery power supply 28, electrical leads 30, 32, and a pair of electrical contacts 34, 36. The electronics package is contained within a housing 38. The combination of the electronics packaging and the housing 38 form the generator 39. The housing 38 includes two lead slots 40, 42 (FIGS. 3 and 4) which provide access to the electrical contacts 34, 36 (FIG. 2). The retainer 16 portion of the applicator includes two electrical leads 44, 46 FIG. 3) that snap into the lead slots 40, 42 on the housing 38 and into the electrical contacts 34, 36 (FIG. 2) and connect the battery supply 28 to the electrodes 12, 14. The teachings of U.S. Pat. No. 5,224,927 are specifically incorporated herein.

Figure 4:
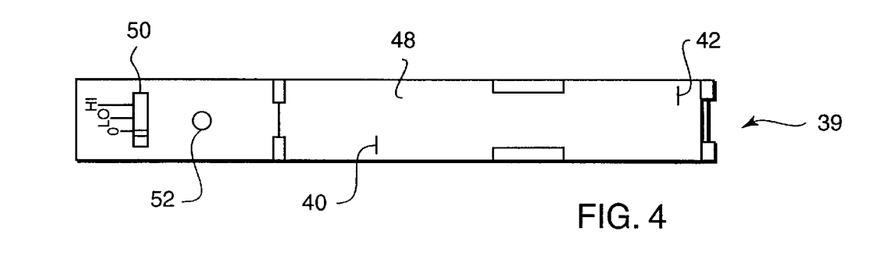
FIG. 4 is a top view of the generator.
Figure 5:
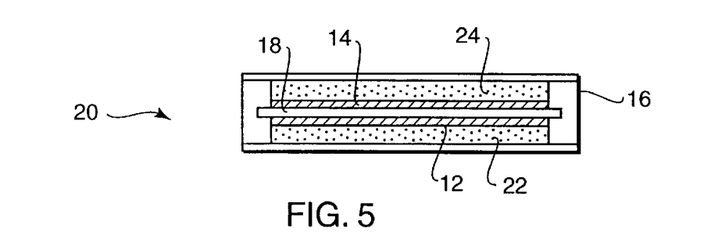
FIG. 5 is a top view of the applicator.

The electronics package may also include an electrical slide switch 50. The switch projects through an upper plastic cover plate 48 of the housing 38. The switch 50 is electrically connected in the housing 38 to the AC generating chip 26. The switch 50 may be selectively moved between a "0" (of position, to either a "LO" (low current or lower rate of ion delivery) or "HI" (high current or higher rate of ion delivery) switch positions.

The function of the switch 50 in FIG. 4 is as follows:
1) The "0" position keeps the device from functioning.
2) The "LO" treatment position infuses aluminum ions at the lowest current level at a continuous, controlled rate.
3) The "HI" treatment position infuses aluminum ions at a current level typically twice as high as the "LO" setting.

A second switch (not shown), similar to the slide switch 50, may also be provided to selectively vary the frequency of the low-frequency AC duty-cycle of the iontophoretic treatment device 10. The low-frequency AC duty-cycle operation of the device is explained below.

An LED test indicator 52 extends from the electronics package within the housing 38 through an appropriate opening in the cover plate 48, and is observable from the top of the iontophoretic treatment device 10 to confirm proper electrical operation of the system for the user. The electronics package may also include a buzzer (not shown) that is connected to a timer in the AC generating chip 26. The timer may be set to sound the buzzer at a time interval, e.g., 10 seconds, in order to provide an indication to the user as to the cumulative treatment time.

Figure 6:
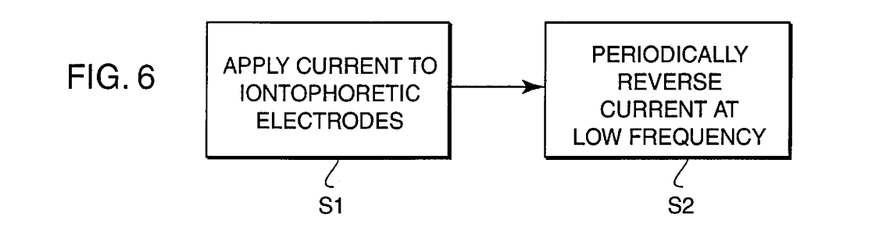
FIG. 6 is a flow chart illustrating an iontophoretic process.

Referring now to FIG. 6, the low-frequency AC duty-cycle process which facilitates the numerous advantages of the present invention is broadly illustrated and defined. In this regard, at step S1, the process calls for applying electrical current to a pair of iontophoretic electrodes of opposite polarity, such as the electrodes 12, 14 in the iontophoretic treatment device 10. In step S2, the electrical polarity and, therefore, the direction of the electrical current flowing between the electrodes 12, 14 and through the patient is periodically reversed, twice per AC cycle. This reversal of current occurs at low frequencies in the substantially critical range of approximately 10 Hz to once every three minutes, or a low frequency limit of approximately 0.0027 Hz, to achieve the advantages previously and subsequently described herein in connection with the practice of the present invention.

Figure 7:
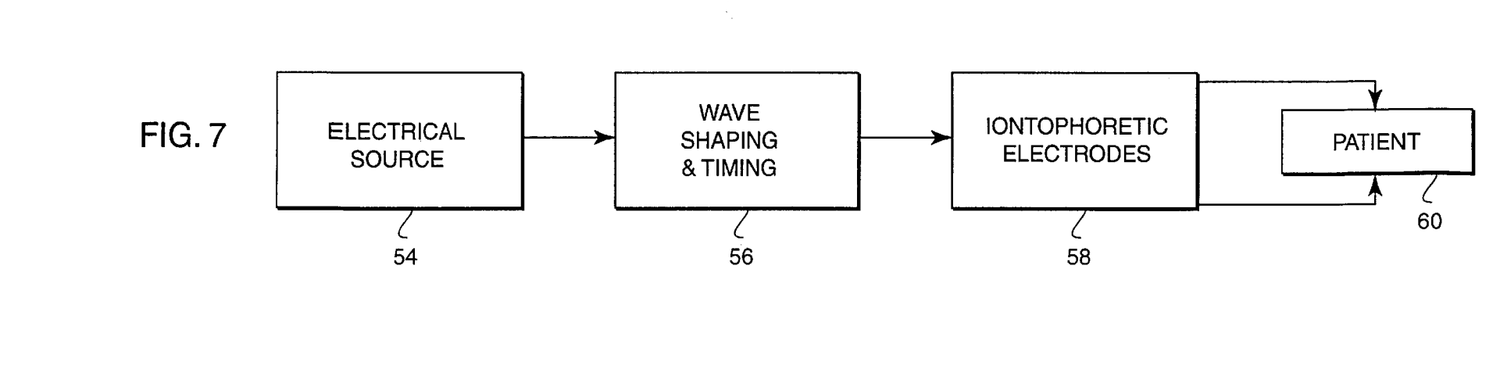
FIG. 7 is a general block diagram of the iontophoretic device of FIGS. 1 and 2.

FIG. 7 is a basic block diagram illustrating the electronics package contained within the housing 38, wherein an electrical source 54 is directed to appropriate wave shaping and timing circuitry 56 for generating the aforedescribed low-frequency AC duty-cycle which is then directed as electrical current to iontophoretic electrodes 58 to infuse aluminum ions into the skin, i.e., the electrical load in the system. It is apparent that the various electrical subsystems indicated in FIGS. 6 and 7 can be implemented readily by those of ordinary skill in the art without the exercise of inventive skill. For example, the system illustrated in FIG. 7 may be implemented, in a presently preferred embodiment of the invention, by the more detailed system shown in FIG. 8.

Figure 8:
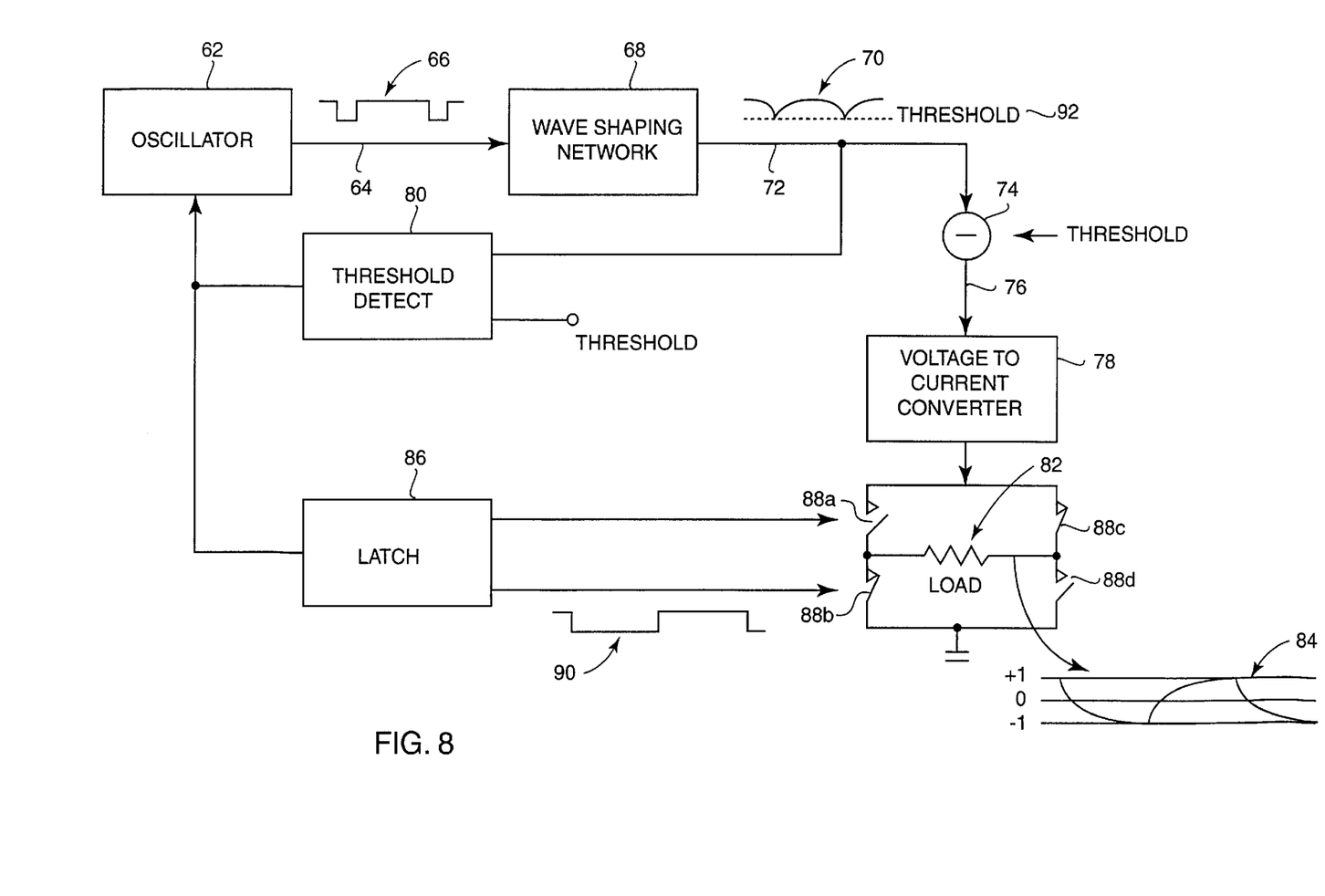
FIG. 8 is a schematic block diagram, including waveforms, of a iontophoretic device.

Referring now to FIG. 8, there is shown a presently preferred embodiment of an overall system for providing a regulated and periodically reversible electrical current into a variable load resistance, i.e., the patient. In the system, the electrical current reverses polarity and direction of flow periodically at a very low frequency. A smooth transition without discontinuity in slope is made between polarities, thus avoiding a shock sensation to the patient when reversing the electrical current. The magnitude and duty cycle of the positive and negative currents are substantially the same. The system utilizes a conventional DC power supply.

The timing of current reversals is determined by an oscillator 62, which produces at its output 64 sharp transitions between two levels, as illustrated by the waveform 66. The electrical output 64 is applied to a wave shaping network 68 to produce gradual electrical transitions, as shown by the output waveform 70 available on line 72. The electrical output of the oscillator 62, and thus the sense of the smoothed waveform, is reversed when the waveform crosses a predetermined threshold 92 determined at junction 74 under the control of a threshold detection subsystem 80. The voltage waveform 70, less the threshold 92, is applied over line 76 to a suitable voltage-to-current converter subsystem 78.

The polarity of the electrical current through a floating load 82, e.g., the patient, reverses at the threshold crossing time, when the instantaneous electrical load current is zero, as illustrated by the waveform 84. A latch subsystem 86 controls a plurality of switches 88a–88d, as shown by the waveform 90, to maintain this polarity until the next threshold crossing. This produces smooth transitions between electrical current levels that are by design, substantially equal in magnitude but opposite in sign. The relatively slow rise and decay evident from leading and trailing edges of the waveform 84 provides the desirable electrical ramping up and down of each half cycle to minimize shock sensations.

The electronics package may provide for a fixed current reversal frequency. If desired, the electrical system may be modified, in a manner well known to those of ordinary skill in the art, to automatically vary the signal frequency periodically. One example of specific electrical circuitry, suitable for implementing the system shown in FIG. 8, is set forth in Appendix A attached hereto and which is specifically incorporated by reference herein.

In operation, the pads 22, 24 are soaked with water to activate the chemicals carried by the pad. The pads 22, 24 are then placed in the retainer 16, one adjacent each of the electrodes 12, 14. The retainer 16 is then placed in the axilla area. The switch 24 is moved from the "0" position to either the "LO" or "HI" position as prescribed below. Electrical current is thus applied to the electrodes 12, 14 by the generator 39 to direct ions into the eccrine duct for sweat control. The aluminum ions from the electrodes 12, 14 and from the chemicals carried by the pads 22, 24 precipitate the skin protein and plug the sweat pores.

In one embodiment of the invention, for treatment of mild cases of excess sweating, the treatment regimen comprises one 10 to 20 second session. The system is optimally operated such that at least one cycle occurs within the session. In another embodiment of the invention, for treatment of severe cases of hyperhidrosis, the treatment regimen may comprise a series of longer sessions, or 10 to 20 second sessions spread over time, depending on the user's tolerance to electrical current at either the "HI" or "LO" setting. For those individuals who are particularly sensitive to electrical current the treatment session may be only at a "LO" setting. For those who can tolerate current well the session may be at a "HI" setting. Upon completion of a treatment session, the iontophoretic treatment device 10 is switched to the "0" position. A variable potentiometer may be substituted for the switch 24 to provide more precise current adjustment.

Figure 3:
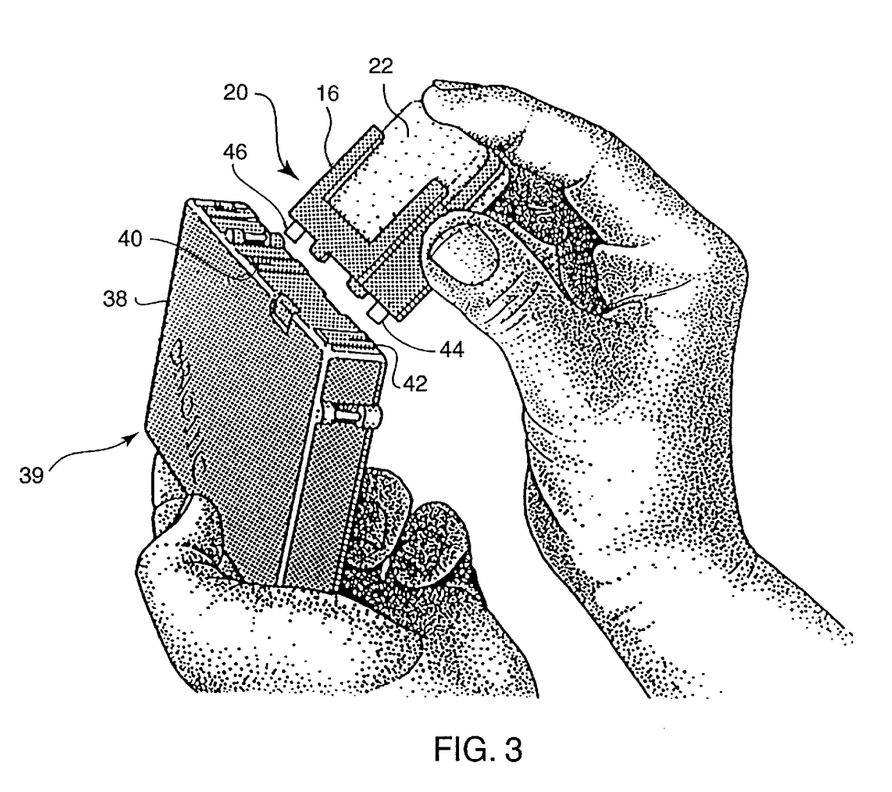
FIG. 3 is a perspective view of the iontophoretic device of FIG. 1, showing the applicator being separated from the generator.

Through repeated use of the device the amount of aluminum ions available for penetration into the skin decreases. Eventually the amount decreases to a point where the device 10 is no longer effective. In accordance with the present invention, the applicator 20 may then be separated from the generator 39, as shown in FIG. 3, and a new applicator 20 installed in its place. In this sense, the applicator may be considered a disposable unit. It is also possible that the chemicals within the pads 22, 24 deplete before the aluminum electrodes 12, 14. In that case, a new set of pads 22, 24 may be installed in the applicator 20.

With the slow AC signal utilized in the system of the present invention, antiperspirant concentration can be increased substantially beyond the two percent level typically present in over-the-counter topical antiperspirants. With a positively charged aluminum ion antiperspirant carried by a pad 22, 24 when the positive half of the AC signal is driving the electrode 12, 14 associated with the pad, then the positive metallic ion component of the antiperspirant is repelled and driven into the skin. The sodium salicylate also contains a negative component, i.e. the salicylate ion. However, when the AC signal swings negative on the other half of the signal, the salicylate negative ion is driven into the skin. This enables substantially increased antiperspirant concentrations.

Since both electrodes are "active" with the simplified arrangement of the present invention, the device can deliver twice the amount of antiperspirant compared to a comparable DC iontophoretic device. For example, if the antiperspirant to be delivered is negative and the signal at one electrode 22, 24 is negative, then that pad delivers the antiperspirant to the skin. Simultaneously, the other electrode is positive and the same antiperspirant does not ordinarily flow.

Enhanced skin permeability occurs through the use of an appropriate salt of salicylic acid, such as sodium salicylate. The salicylate is electrically delivered into the treatment site and greatly lowers skin resistance and increases skin permeability thereby allowing for more effective iontophoretic treatment. In a preferred embodiment of the invention, the salicylate is carried, along with the antiperspirant chemicals, by the pads and is accordingly driven into the treatment region along with the antiperspirant chemicals.

Figure 9:
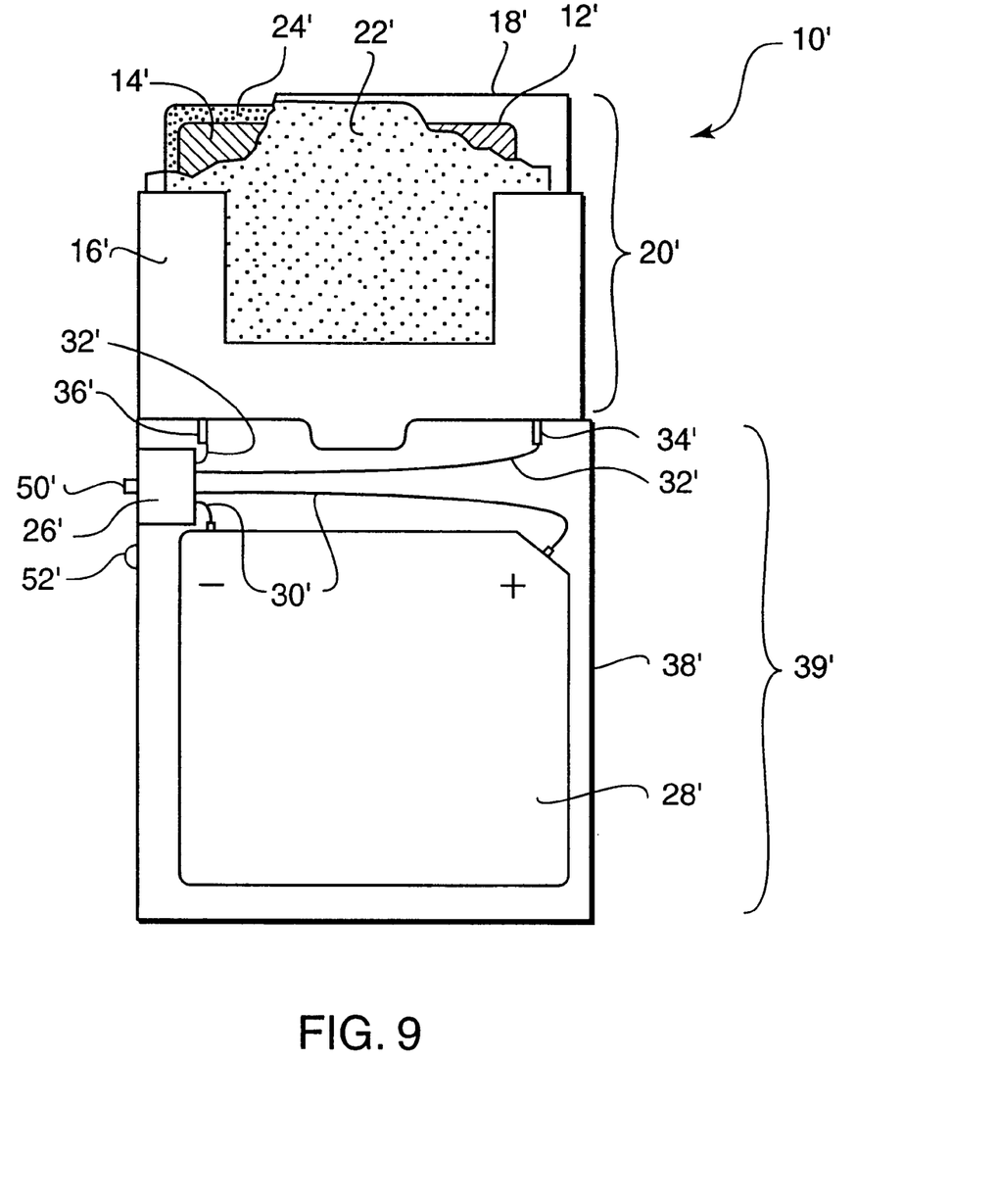
FIG. 9 is a plan view of another presently preferred embodiment of an iontophoretic device, with a side cover of the generator being removed and portions of the applicator being broken away to illustrate internal structure.

With reference to FIG. 9, there is shown a second configuration of a more compact iontophoretic device 10' which incorporates aspects of the present invention. Except for the size of the generator 39' and the battery power supply 28' included therein, this configuration of an iontophoretic device 10' is generally identical to the iontophoretic device 10' of FIGS. 2 through 5. For ease in correlating the two configurations, the numerals associated with elements of the second configuration are the same as those of the first configuration except that they are primed.

The second configuration of the iontophoretic device 10' is ideally suited for daily, short duration treatments, such as the 10 to 20 second treatment period previously described. The applicator 20' is identical to that of the first configuration device 10 (FIG. 2) and is removable from the generator 39' in the same manner as the first configuration. The battery power supply 28' (FIG. 9) comprises one 9V battery that drives the AC generator 26'. In a preferred embodiment of the second configuration, to maintain overall cost at a minimum, the frequency control present in the first configuration is absent, and an appropriate value of the frequency parameter is set during manufacture and prior to delivery to the ultimate user. With regard to frequency, the AC generator 26' is configured to ensure that at least one current reversal cycle occurs during the 10 to 20 second treatment period.

Hence, those concerned with development and use of hyperhidrosis treatment systems will appreciate that the present invention satisfies a long existing need in the art for a system capable of administering deep-penetrating iontophoretic application of antiperspirant chemicals to the human body in a short period of time, operates at a relatively low power rating and is conducive to daily use. Of course, it will be apparent that the sweat control system may be applied to any portion of the anatomy where sweating is a problem.

It will be apparent from the foregoing that, while particular forms of the invention have been illustrated and described, various modifications can be made without departing from the spirit and scope of the invention. Therefore, it is not intended that the invention be limited, except as by the appended claims.

What is claimed is:

1. A sweat control system for effecting iontophoresis at a region of tissue, said device comprising:
    a source of electric current;
    a controller;
    a pair of electrodes mounted in generally close proximity to one another and separated by an insulating member, said electrodes carry an antiperspirant element and are responsive to said source of electrical current through said controller, one of said electrodes being connected to said source of electrical current and arranged to act primarily as a cathode, and the other of said electrodes being connected to said source of electrical current and arranged to act primarily as an anode; and
    a pair of pads, each of said pads positioned in adjacent contact with one of said electrodes, each of said pads carrying sodium salicylate and an aluminum-based antiperspirant;
    wherein said electrodes are sized and arranged so that the tissue to be treated can extend across said insulating member and simultaneously contact both of said pads.

2. The device of claim 1 wherein the antiperspirant consists of one of either aluminum-chlorohydrate or aluminum-zirconium.

3. The device of claim 1 wherein the electrodes are formed of sheet stock metal having an irregular, nonsmooth, surface.

4. The device of claim 3 wherein the electrodes comprise sandblasted sheet stock metal.

5. The device of claim 3 wherein the electrodes comprise powdered metal formed on said sheet stock metal.

6. The device of claim 3 wherein the electrodes comprise aluminum oxide.

7. The device of claim 1 wherein the sheet stock metal consists of aluminum, aluminum alloy, magnesium or magnesium alloy.

8. A device for applying iontophoresis treatment to a region of a biological subject, said device comprising:
    first and second electrodes mounted in generally close proximity to one another and separated by an insulating member;
    a pair of pads, each of said pads positioned in adjacent contact with one of said electrodes, each of said pads carrying an antiperspirant and sodium salicylate, wherein said electrodes are sized and arranged so that the region to be treated can extend across said insulating member and simultaneously contact both of said pads;
    an electrical energy source for conducting an electrical current through the region in a first direction from the first electrode to the second electrode; and
    a controller for intermittently reversing, at a relatively low frequency which prevents skin damage, between approximately 20 times per second and approximately once every three minutes, the polarity of said electrodes to cause said electrical current to flow in a second direction opposite to said first direction.

9. The device of claim 8 wherein the antiperspirant is aluminum based.

10. The device of claim 9 wherein the antiperspirant consists of one of either aluminum-chlorohydrate or aluminum-zirconium.

11. The device of claim 10 wherein the percentage of aluminum-chlorohydrate or aluminum-zirconium contained within the antiperspirant is greater than 2%.

12. The device of claim 8 wherein the antiperspirant comprises an anticholinergic.

13. An applicator for providing the chemical materials necessary to affect iontophoresis treatment to a region of a biological subject, said applicator responsive to an AC waveform provided by a generator, said applicator comprising:
    first and second electrodes mounted in generally close proximity to one another and separated by an insulating member, said electrodes responsive to said AC waveform; and
    a pair of pads, each of said pads positioned in adjacent contact with one of said electrodes, each of said pads carrying an antiperspirant and a salt of salicylic acid, wherein said electrodes are sized and arranged so that the region to be treated can extend across said insulating member and simultaneously contact both of said pads.

14. The applicator of claim 13 wherein the first and second electrodes are responsive to the AC waveform such that the electrodes are of opposite polarities.

15. The applicator of claim 13 wherein the pads comprise a material containing the antiperspirant.

16. The applicator of claim 13 wherein the pads are formed of a fiber and the antiperspirant is saturated into the pads.

17. The device of claim 13 wherein the antiperspirant comprises aluminum based chemicals.

18. The device of claim 17 wherein the antiperspirant comprises aluminum-chlorohydrate.

19. The device of claim 17 wherein the antiperspirant comprises aluminum-zirconium.

20. The device of claim 13 wherein the antiperspirant comprises an anticholinergic.

21. The device of claim 13 wherein the electrodes are formed of sheet stock metal having an irregular, nonsmooth, surface area.

22. The device of claim 21 wherein the sheet stock metal consists of aluminum, aluminum alloy, magnesium, or magnesium alloy.

23. The device of claim 21 wherein the electrodes comprise sandblasted sheet stock metal.

24. The device of claim 21 wherein the electrodes comprise powered metal formed on said sheet stock metal.

25. The device of claim 15 wherein the electrodes comprise aluminum oxide.

26. A method of iontophoretic infusion of antiperspirant substances into a biological subject, comprising the steps of:

locating a pair of electrically conductive electrodes adjacent a surface of said subject to be treated;

placing at least one antiperpirant substance and sodium salicylate between at least one of said electrodes and said surface of said subject to be treated; and conducting an A.C. electrical current through said surface of said subject for a set duration of time, said current passing through said surface in a first direction from a first of said electrodes to a second of said electrodes on said subject.

27. The method of claim 26, including:

periodically and regularly reversing, at a relatively low frequency, between approximately 20 times per second and approximately once every three minutes, the polarity of said electrodes to cause said electrical current to flow in a second direction opposite to said first direction.

28. The method of either claim 26 or claim 27 wherein said set time duration is between 10 and 20 seconds and said low frequency is such that the polarity of said electrodes is reversed at least once during said set time duration.

29. The method of either claim 26 or claim 27 wherein the electrodes are formed of sheet stock metal having an irregular, nonsmooth, surface area.

30. The method of claim 29 wherein the sheet stock metal consists of aluminum, aluminum alloy, magnesium, or magnesium alloy.

31. The method of either of claims 26 or 27 wherein the antiperspirant comprises an aluminum-based chemical.

32. The device of claim 31 wherein the aluminum-based chemical consists of one of either aluminum-chlorohydrate or aluminum-zirconium.

33. A sweat control treatment system, comprising:

a source of electric current;

a controller;

electrode means connected to said controller; and a preparation of sodium salicylate and an antiperspirant adjacent said electrode means and adapted to be delivered to a treatment site to enhance delivery of additional metallic ions to said treatment site.

34. The device of claim 33 wherein the preparation further includes an aluminum-based antiperspirant.

35. The device of claim 34 wherein the antiperspirant consists of one of either aluminum-chlorohydrate or aluminum-zirconium.

36. The device of claim 33 wherein said electrode means are formed of sheet stock metal having an irregular, nonsmooth, surface.

37. The device of claim 36 wherein said electrode means comprises sandblasted sheet stock metal.

38. The device of claim 36 wherein said electrode means comprises powdered metal formed on said sheet stock metal.

39. The device of claim 36 wherein said electrode means comprises aluminum oxide.

40. The device of claim 33 wherein the sheet stock metal consists of aluminum, aluminum alloy, magnesium or magnesium alloy.

41. In a system for sweat control, the combination comprising:

an iontophoretic delivery unit;

and a preparation of an antiperspirant including a salt of salicylic acid and any one of an anticholinergic substance aluminum chlorohydrate and aluminum-zirconium adapted for delivery to a subject by said iontophoretic delivery device.

42. A system as recited in claim 41 wherein said iontophoretic delivery device provides a low frequency A.C. signal to deliver said preparation.

43. A system as set forth in claim 42 wherein said A.C. signal is in the range of 10 Hz–0.0027 Hz.

44. A system as recited in either of claims 41, 42 or 43 wherein said preparation includes sodium salicylate.

45. A method for sweat control, comprising:

providing a preparation of an antiperspirant including a salt of salicylic acid and any one of an anticholinergic substance aluminum chlorohydrate and aluminum-zirconium adapted for delivery to a subject by iontophoresis; and delivering said preparation to a selected site on said subject by iontophoresis.

46. A method as recited in claim 45, wherein said iontophoresis includes delivery by low frequency A.C. current.

47. For use with an iontophoretic hyperhidrosis control device, the combination comprising:

a mixture of an antiperspirant including a salt of salicylic acid adapted for delivery by said iontophoretic delivery device; and metal output electrodes having extended surfaces.

48. A combination as set forth in claim 47, wherein the antiperspirant comprises aluminum based chemicals.

49. A combination as set forth in claim 47, wherein the antiperspirant comprises aluminum chlorohydrate.

50. A combination as set forth in claim 47, wherein the antiperspirant comprises aluminum-zirconium.

51. A combination as set forth in claim 47, wherein the antiperspirant comprises anticholinergic.

52. A combination as set forth in claim 47, wherein the electrodes are formed of sheet stock metal having an irregular, nonsmooth, surface area.

53. A combination as set forth in claim 52, wherein the sheet stock metal consists of aluminum, aluminum alloy, magnesium, or magnesium alloy.

54. A combination as set forth in claim 52, wherein the electrodes comprise sandblasted sheet stock metal.

55. A combination as set forth in claim 52, wherein the electrodes comprise powdered metal formed on said sheet stock metal.

56. A combination as set forth in claim 52, wherein the electrodes comprise aluminum oxide.

* * * * *

UNITED STATES PATENT AND TRADEMARK OFFICE
CERTIFICATE OF CORRECTION

PATENT NO.    : 6,223,076 B1  
DATED         : April 24, 2001  
INVENTOR(S)   : Robert Tapper Page 1 of 1

It is certified that error appears in the above-identified patent and that said Letters Patent is hereby corrected as shown below:

Column 11, claim 25,
Line 8, change "15", to read -- 13 --.

Column 11, claim 34,
Lines 54 and 55, delete entire claim 34, replace with amended claim as follows:
-- 34. The device of claim 33, wherein the antiperspirant is aluminum-based. --.

Signed and Sealed this

Eighth Day of January, 2002

*Attest:*

JAMES E. ROGAN

UNITED STATES PATENT AND TRADEMARK OFFICE
CERTIFICATE OF CORRECTION

PATENT NO. : 6,223,076 B1
DATED : April 24, 2001
INVENTOR(S) : Robert Tapper

Page 1 of 1

It is certified that error appears in the above-identified patent and that said Letters Patent is hereby corrected as shown below:

<u>Column 11, claim 25,</u>
Line 8, change "15", to read -- 13 --.

<u>Column 11, claim 34,</u>
Lines 54 and 55, delete entire claim 34, replace with amended claim as follows:
-- 34. The device of claim 33, wherein the antiperspirant is aluminum-based. --.

This certificate supersedes Certificate of Correction issued January 8, 2002

Signed and Sealed this

Fifth Day of February, 2002

Attest:

Attesting Officer

JAMES E. ROGAN
*Director of the United States Patent and Trademark Office*